United States Patent [19]

Rosenberg

[11] Patent Number: 4,712,999
[45] Date of Patent: Dec. 15, 1987

[54] CONVERTIBLE, SELF-LIGATING, ARCHWIRE POSITIONING ORTHODONTIC BRACKET

[76] Inventor: Farel Rosenberg, 10535 Wilshire Blvd., Los Angeles, Calif. 90024

[21] Appl. No.: 905,409

[22] Filed: Sep. 10, 1986

[51] Int. Cl.⁴ .................................................. A61C 7/00
[52] U.S. Cl. ........................................ 433/8; 433/11; 433/13
[58] Field of Search ........................... 433/11, 13, 8

[56] References Cited

U.S. PATENT DOCUMENTS

| | | | |
|---|---|---|---|
| 3,084,437 | 4/1963 | Neger | 433/11 |
| 3,091,857 | 6/1963 | Rubin et al. | 433/11 |
| 4,103,423 | 8/1978 | Kessel | 433/10 |
| 4,355,975 | 10/1982 | Fujita | 433/17 |
| 4,498,867 | 2/1985 | Kesling | 433/17 |
| 4,551,094 | 11/1985 | Kesling | 433/17 |
| 4,559,012 | 12/1985 | Pletcher | 433/10 |

*Primary Examiner*—Robert Peshock
*Attorney, Agent, or Firm*—Gilbert Kivenson

[57] ABSTRACT

An orthodontic bracket with self-ligating features is described. A cover plate is rotatably attached to the bracket base. Turning of the cover plate to the open position provides access to an archwire slot. After archwire placement, returning of the cover plate to its closed position achieves various degrees of play and seating depending on archwire size and cover plate configuration. The over plate promotes cleanliness and provides cosmetic advantages.

7 Claims, 10 Drawing Figures

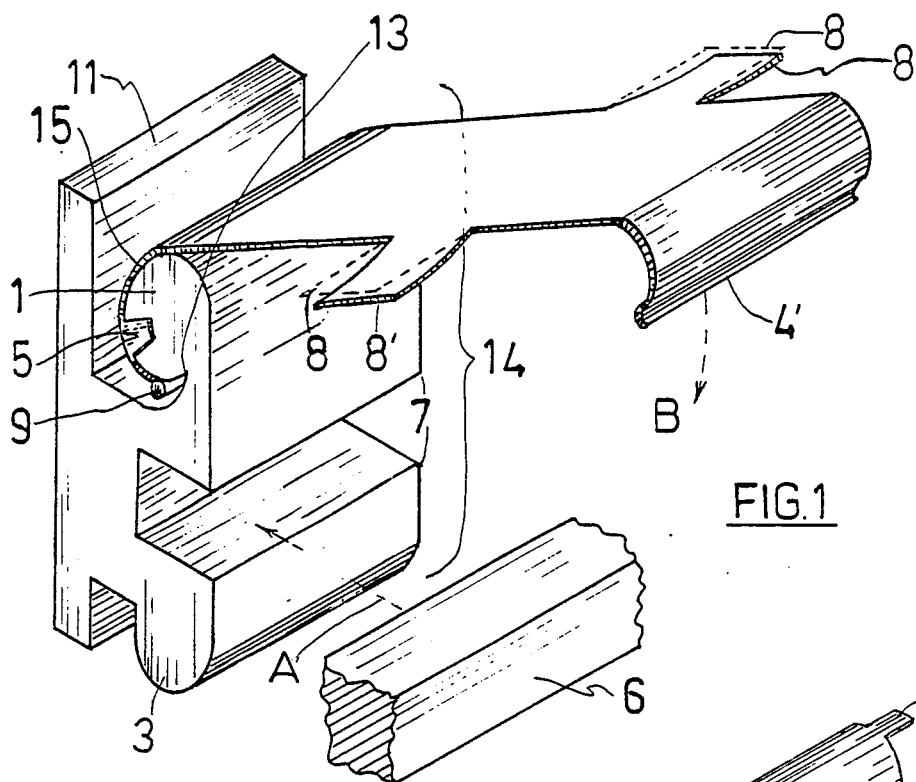
FIG.1
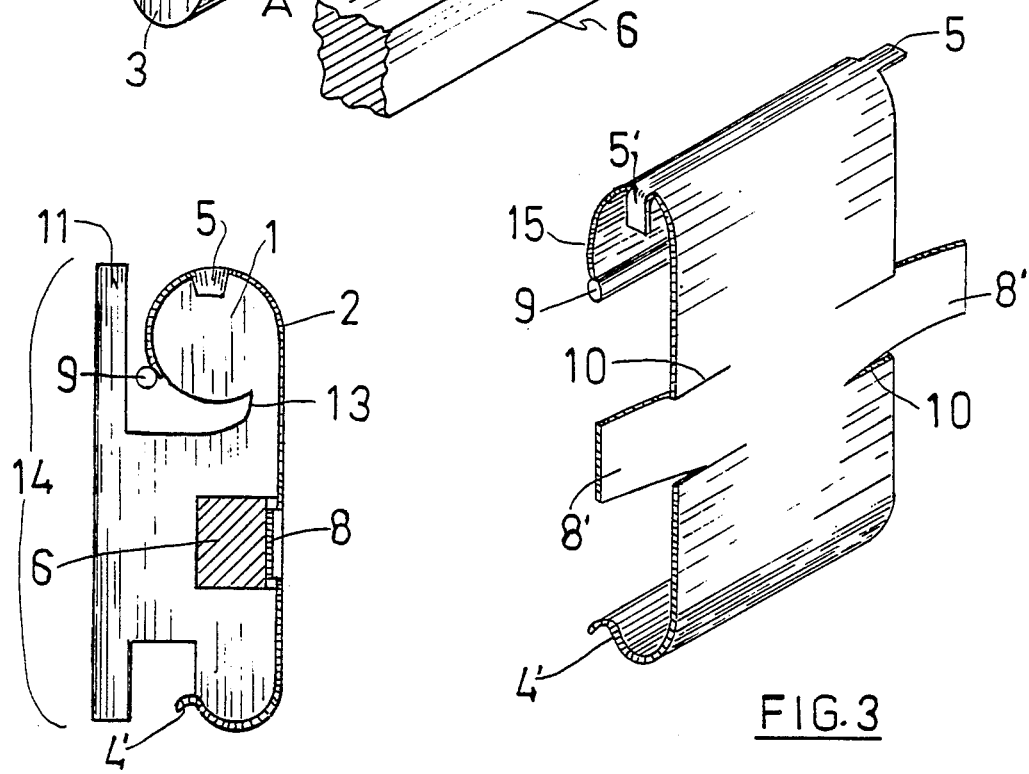
FIG. 2
FIG. 3

CONVERTIBLE, SELF-LIGATING, ARCHWIRE POSITIONING ORTHODONTIC BRACKET

In orthodontic practice there has been a steady improvement in the structures used in a patient's mount. The trend has been to miniaturization, enhanced appearance of the apparatus from a cosmetic viewpoint and increased simplification of installation and removal. At present small, slotted brackets are employed. These are bonded directly to the front or rear surfaces of the teeth. A curved archwire (conforming to the patient's dental arch) is formed of a special alloy, pretensioned by the orthodontist to produce desirable movement of the teeth and fitted into the slots in the brackets. After the archwire is tied down to each bracket by a much finer "ligating" wire or elastic "doughnut", the pretensioning forces come into play to achieve the desired tooth movement. Rotation wedges or like devices are used for teeth which are severely rotated. The finess of the ligating wire makes necessary considerable skill on the part of the orthodontist and long chair time for the patient. It is also normally required that the archwire be removed for retensioning or replacement a number of times during the course of the treatment. The ligating process must be repeated each time.

It is sometimes required that the archwire have play, i.e. that it be not fully seated. A loose ligation is therefore required. In other instances the archwire must be fully seated and have no play. This requires a tight ligation. In addition the ligations are sometimes broken during chewing or brushing and must be replaced. The rough edges generated by an accidental break or the "pigtails" which terminate the ligation wires create a dental emergency with inconvenience and discomfort for the patient. Often the surfaces of the tied, fine ligating wires or rotation wedges act as food traps which are hard to keep clean. When elastic "doughnuts" are used, they discolor and rapidly lose their elasticity. Their efficiency in securing the archwire to the base of the bracket falls off and they become ineffective. It would therefore by highly desirable if each bracket would incorporate a rapid clamping and unclamping device i.e. be "self-ligating" and also allow play or full seating of the archwire. In this way the use of ligating wires, elastic "doughnuts" and rotation devices could be greatly reduced.

Prior art directed to this problem has resulted in complex structures which are expensive to manufacture or contain separable parts which can accidentally be swallowed or are difficult to apply. Self-ligating brackets have been devised by Pletcher (U.S. Pat. Nos. 4,371337; 4,077,126; 4,419,178,; 3,444,621), Fostee (U.S. Pat. No. 4,268,249), Brader (U.S. Pat. No. 3,327,393), and Fujita (U.S. Pat. No. 4,355,975). My present invention as well as my copending "An Orthodontic Bracket Having Archwire Seating and Locking Mechanism", Ser. No. 852,452, are easily fabricated, convertible and easily applied.

SUMMARY OF THE INVENTION

This invention relates to an orthodontic bracket and its cover plate with built-in provision for archwire play, seating, rotation and in-out tooth movement (using adjacent teeth) after locking. The bracket is an assembly of two components: a base and a cover plate. The base contains an archwire slot in its center and a transverse, semi-cylindrical section on both its upper and lower ends. The cover plate is formed into a hollow, semi-cylinder at its upper end to make up a hinge with the upper base, semi-cylindrical section. A clip at the lower end of the cover plate permits a firm hold on the lower semi-cylindrical section of the base. In the center of the cover plate is a flat spring or two indentations. When the plate is rotated on the hinge to a closed position flat against the front of the base, the clip of the cover plate engages and locks over the lower semi-cylindrical section while the flat spring or pair of indents exert adjustable pressure on the archwire in its slot.

In use, an archwire is introduced into the slot of a tooth-mounted bracket; the cover plate is then swung into its closed position. The flat spring or pair of indents is brought to bear on the archwire by a desired amount and the cover plate locked into position. Whe the archwire is to be removed, the end of a sharp instrument is brought under the clip and it is sprung free. The plate can now be rotated open through 120 or more degrees so as to allow free access to the slot. Hinge friction or gravity serves to hold the cover plate open while the orthodontist alters the archwire prior to reinstallation. The plate serves to block the entry of food particles while it is closed. It may be coated with a pigment similar in color to tooth enamel or made of a synthetic tooth-colored material for cosmetic blending. In the above description the cover plate swings out and away from the base to reveal the slot. In another embodiment of the invention the cover plate is mounted by a rivet perpendicular to the base. In this embodiment the opening takes place in a plane parallel to the base.

DESCRIPTION OF THE DRAWINGS

FIG. 1 is an isometric view of the invention showing the base attached one version of the cover plate with the latter in an open position.

FIG. 2 is a side view of the invention of FIG. 1 showing an archwire being held in place by a closed and latched cover plate.

FIG. 3 is an isometric view of a second variation of a cover plate prior to assembly to a slotted base.

DESCRIPTION OF THE INVENTION

Figure 4:
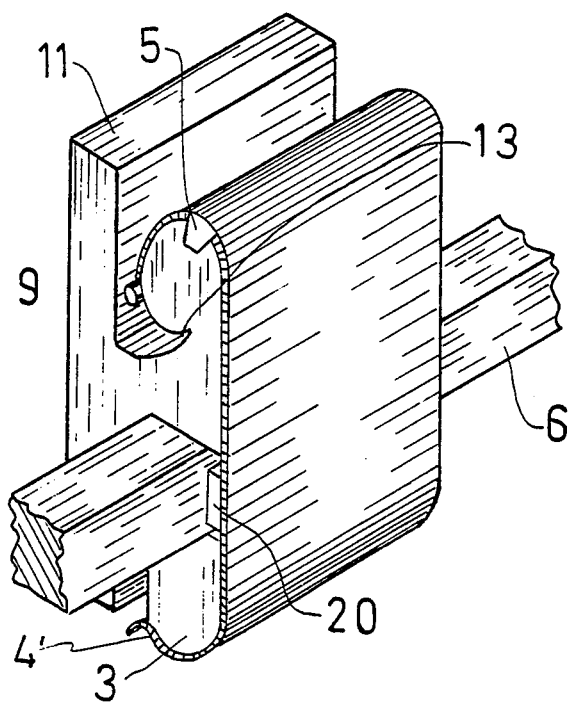
FIG. 4 is an isometric view of the invention with another version of a cover plate in closed position holding an archwire within its slot to its base.

The operation of the invention will be explained with reference to FIGS. 1 through 10. The bracket body 14 (FIGS. 1 and 2) incorporates the semi-cylindrical segment 1 at its upper end and the semi-cylindrical segment 3 at its lower end, both integral with the base 11. The semi-cylindrical segment 1 is undercut at 13 as shown in FIGS. 1 and 2. A slot 7 is provided to fit an archwire 6. The cover plate is rolled at one end into the semi-cylindrical form 15 and is provided with the confining tabs 5'. A cylindrical bar 9 is attached or may be formed of the material of the flat plate. Leaf springs 8' are formed from the tabs 8 by bending.

Assembly of the bracket body to the cover plate is accomplished by sliding the semi-cylindrical portion 15 of the plate over the semi-cylindrical segment 1 and bending down the tab 5. FIGS. 1 and 3. The tab 5' is bent during manufacture. This confines the plate laterally while permitting rotation in the vertical direction. The position of the spring 8' is such as to be in alignment with the slot 7 when the plate is rotated to a closed position.

In use, brackets of this construction are bonded to the teeth as in prior art. After the preflexed archwire 6 is successively pushed into each slot, step A in FIG. 1, each cover plate 2 is then rotated and its clip 4' is forced over the lower semi-cylindrical segment 3, step B. This brings the leaf springs 8' to bear on the archwire, locking it and seating it to its base (FIGS. 1 and 2). It is also possible by selection of archwire size and spring tension to bring about play when desired. If the slot 7 is of graded depth (laterally), the bracket cover plate can also be used to apply tooth rotating forces. The cover plate 2 and other parts of the bracket can be finished in various shades of white so as to decrease the visibility of the bracket when installed. It can also be made of synthetic, tooth-colored materials such as plastics.

The undercut 13, shown in FIGS. 1, 2 and 4 retains the cylindrical bar 9 when cover plate 2 is in the open position. Frictional force or gravity (depending on the initial positioning of the bracket when it is cemented on to a tooth) thus keeps each cover plate open so that the orthodontist has adequate accessibility to all the slots.

In the cover plate construction pictured in FIG. 4 a block 20 of an inert material such as Teflon or Nylon is attached to the underside of the cover. When the cover plate is closed and locked, the resulting flexion forces 20 against archwire 6, again locking and seating it. This effect could also be accomplished by indenting the cover plate in its central region to create a notch in line with the archwire slot so that the high side of the notch enters the slot. Depending on the size of the archwire and the depth of the indentation, play of the archwire or solid contact may be achieved.

Figure 5:
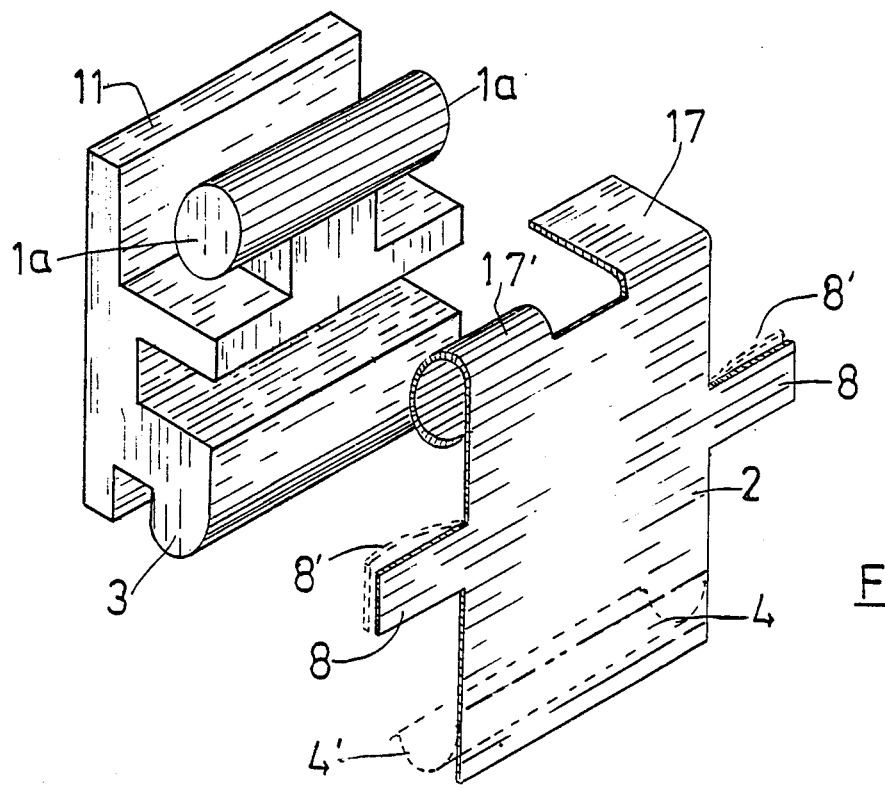
FIG. 5 is an isometric view of a second embodiment of the invention prior to assembly.
Figure 7:
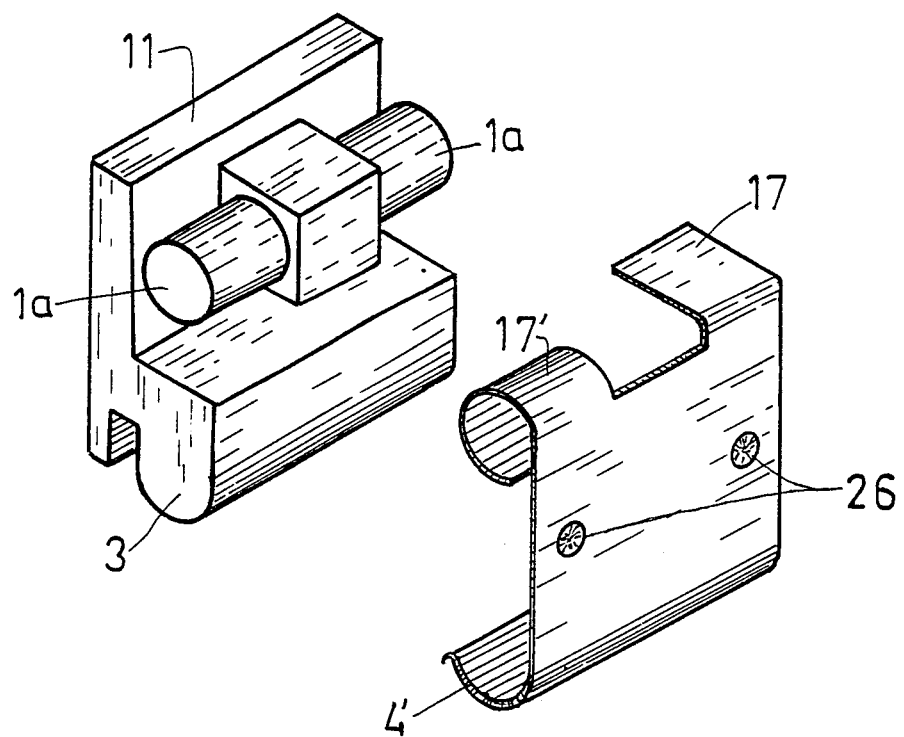
FIG. 7 is an isometric view of a simplified version of the embodiment of FIG. 5.

The bracket and cover plate shown in FIGS. 5 and 7 make use of an extended upper cylindrical section 1a in the bracket body and the tabs 17 on the cover plate. The tabs 17 are formed into the hollow cylinders 17' which together with the extended cylindrical section 1a make up a hinge on which cover plate 2 can rotate. The advantage of this embodiment is the provision of a larger angle of opening of the cover plate and increased accessibility to the slot. The hollow cylinders 17' are made sufficiently close fitting to cylindrical section 1a that the cover plate is held at any angle of opening by friction or gravity.

Figure 6:
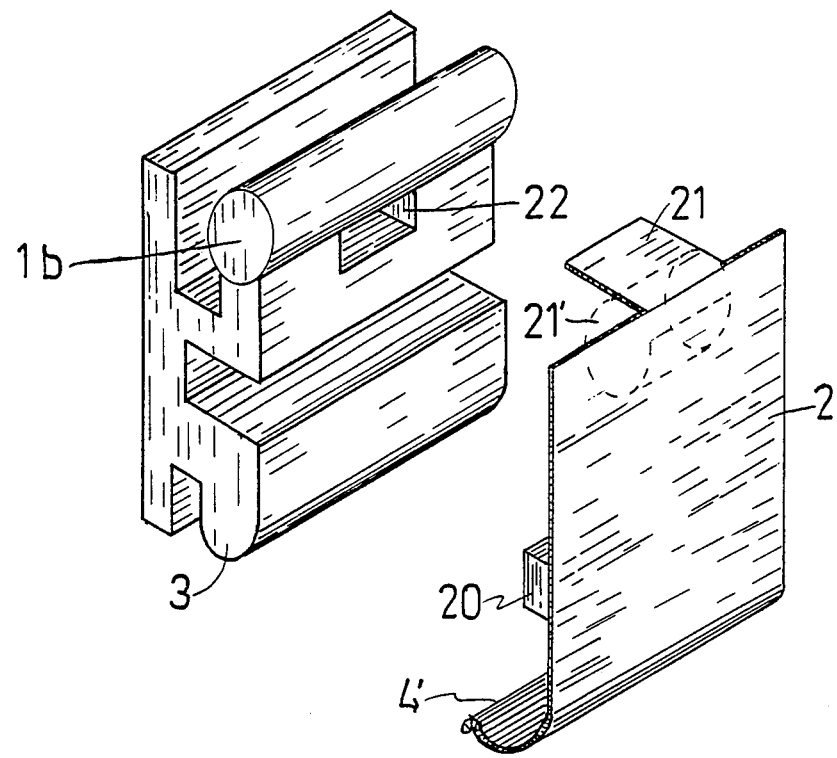
FIG. 6 is an isometric view of a third embodiment of the invention.

Increased angle of opening can also be achieved by the embodiment of FIG. 6. An aperture 22 is formed in the support portion of the upper semi-cylindrical section 1b. A central tab 21 is shaped into the hollow cylinder 21' which fits around the central section of 1b and emerges through aperture 22. Again the fit is such as to retain the cover plate by friction or gravity at any desired angle of opening.

FIG. 7 illustrates a simplified version of the embodiment of FIG. 5. A central support block 33 serves as a mounting for the cylindrical sections 1c and an upper surface of the archwire slot.

The unlocking of clip 4' from the lower semi-cylindrical sections 3 of any of the embodiments of FIGS. 1 through 6 is done by inserting a scaler pick or similar dental tool behind the clip and pulling it away from the bracket. This frees the cover plate.

Figure 8:
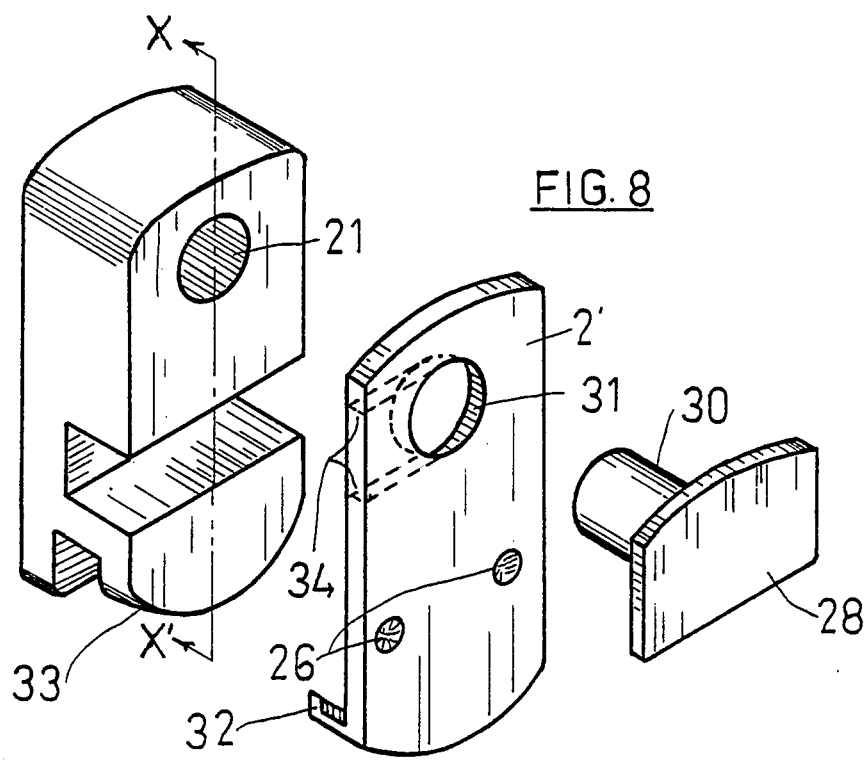
FIG. 8 is an isometric view of a fourth embodiment of the invention prior to assembly.
Figure 9:
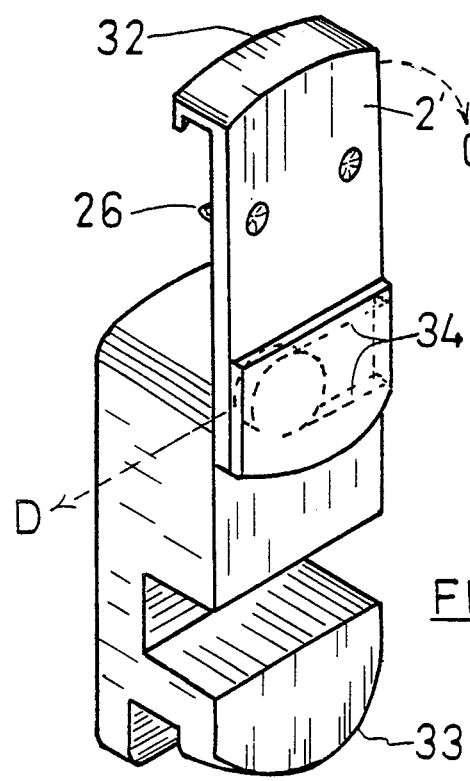
FIG. 9 is an isometric view of the embodiment of FIG. 8 assembled and in an open position.
Figure 10:
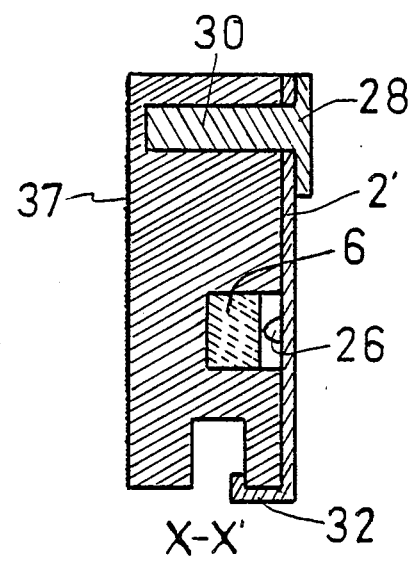
FIG. 10 is a cross section of the embodiment of FIG. 8 taken along the line X—X'.

FIGS. 8, 9 and 10 illustrate an embodiment of the invention in which the cover plate opens parallel to the face of the bracket. The cover plate 2' is held in place by the rivet 30 which is shrink fitted into the hole 2. The cover plate turns on the rivet in the open position shown in FIG. 9. The indentations 26 will contact an appropriately sized archwire and provide seating force, while allowing smaller archwires the necessary play often required in the beginning stages of treatment. To use a fixed diameter or linear dimension of archwire requires various cover plate having a gradation of indent depths. Rotation may be accomplished by the use of a varying-depth slot and cover plates having indents of unequal length. The underside of the cover plate may be color coded for indentification of the indent depth. After the archwire is placed in the slot 7, the cover plate is rotated in the direction C to close the bracket slot, lock the cover plate and secure the archwire. The segment 32 engages the rounded surface 33 to hold the cover closed.

An additional feature of the embodiment shown in FIGS. 8, 9 and 10 may be added by cutting the slot 34 in the cover plate. This slot will permit the removal of the cover plate with the bracket bonded to a tooth and its replacement with a plate having longer or shorter indentations to accommodate various sizes of archwires. The embodiments of FIGS. 1 through 7 can also be modified to incorporate partial hinge cylinders to permit removal and replacement of the cover plate.

The present invention, used in combination over two or more teeth, can provide in and out (i.e. tongue to cheek) orthodontic movements.

The construction of the invention is such that the cover plate cannot unlock or be separated from its hinge during mastication or brushing.

The cover plate prevents accummulation of food particles within the bracket base while its smooth, tooth-colored surface promotes patient comfort and acceptance.

The rear surface of the base 37 in FIG. 10 is of mesh design to facilitate effective cementing to a tooth as in prior art.

What I claim is:

1. An orthodontic bracket assembly comprising:
   a. a base structure having transverse and integral upper and lower semi-cylindrical extensions and also containing a transverse slot between said extensions to receive an archwire;
   b. a cover plate formed at both ends into semi-cylindrical sections, the top cylindrical section being of greater circumference and incorporating a tab at each side and adapted to slide over the said top semicylindrical extension and thus act as a hinge, the lower semi-cylindrical section acting as a clip to fit over and lock with the lower semi-cylindrical extension, said cover plate being able to remain in any open position by friction in the hinge;
   c. an archwire seating member incorporated in the cover plate so as to be aligned with the slot in the base structure when the cover plate is rotated to a closed position;
   whereby the cover plate can be rotated into the open position, an archwire introduced into the slot and the cover plate rotated closed until said clip engages with the lower semi-cylindrical extension, forcing the seating member against the archwire and achieving various degrees of play and seating against the bottom of the slot depending on the archwire size and configuration and the size of the seating member; conversely disengaging the clip permits the cover plate to be rotated into its open position thus unlocking the archwire, the process being easily repeatable for the number of cycles required during the course of the treatment without the bracket being subject to accidental opening and disassembly during normal activities by the patient, said tabs being bent at right angles to the rest of the plate thus confining the plate axially with respect to the semi-cylindrical extensions and restricting its movement to a radial direction.

2. An orthodontic bracket assembly as described in claim 1 in which the archwire seating member is a pair of springs made from tabe initially formed into the cover plate, said pair of springs being augmentable in length by extending cuts made into the body of the cover plate.

3. An orthodontic bracket assembly as described in claim 1 in which the seating member is a block attached to the rear surface of the cover plate and achieves various degrees of play and seating of the archwire against the bottom of the slot depending on archwire size and block thickness.

4. An orthodontic bracket as described in claim 3 in which the seating member is a "V" shaped indentation pressed into the cover plate, the apex of said indentation approaching contact with an archwire of appropriate size when the cover is closed, thus achieving various degrees of play and locking depending on the depth of said "V" shaped indentation.

5. An orthodontic bracket as described in claim 4 in which the seating member is comprised of a pair of conical indentations in the cover plate extending below the surface of the cover plate and approaching contact with an archwire or appropriate size when the cover is closed and useable with a slot of varying lateral depth for tooth rotation and useable in conjunction with similar brackets on adjoining teeth for in-out tooth movement.

6. An orthodontic bracket assembly comprising:
   a. a base structure having transverse and integral upper and lower semi-circular extensions, containing a transverse slot between said extensions to receive an appropriately sized archwire, and a cylindrical cavity through the upper base structure with axis perpendicular to the base structure;
   b. a rivet which can be fitted into said cylindrical cavity;
   c. a cover plate containing a centrally positioned hole near one end to be suspended on and be rotatable about the axis of said rivet, the cover plate being provided with indentations extending below its surface various distances to make adjustable degrees of contact with said archwire and a curved segment at its other end to engage the lower, semicircular extension in a locking relationship;
   whereby the turning of the cover plate on a plane parallel to that of the base opens the transverse slot to permit the insertion of an archwire and, subsequently, turning of the cover plate in the opposite direction encloses said archwire and achieves various degrees of play against the bottom of the transverse slot as the cover plate locks.

7. An orthodontic bracket assembly as decribed in claim 6 in which the cylindrical cavity in said cover plate is cut so that it communicates with one edge of the cover plate permitting removal and replacement of the plate during the period of orthodontic treatment when this becomes desirable.

* * * * *